United States Patent
Toida (10) Patent No.: US 6,594,290 B2
(45) Date of Patent: Jul. 15, 2003

(54) DYNAMIC CHANGE DETECTING METHOD, DYNAMIC CHANGE DETECTING APPARATUS AND ULTRASONIC DIAGNOSTIC APPARATUS

(75) Inventor: Masahiro Toida, Kawasaki (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 82 days.

(21) Appl. No.: 09/859,460

(22) Filed: May 18, 2001

(65) Prior Publication Data

US 2002/0009103 A1 Jan. 24, 2002

(30) Foreign Application Priority Data

May 23, 2000 (JP) ........................................ 2000-151135

(51) Int. Cl.$^7$ .................................................. H01S 3/10
(52) U.S. Cl. ...................................................... 372/28
(58) Field of Search ................................ 356/477, 484, 356/345; 250/343; 372/28

(56) References Cited

U.S. PATENT DOCUMENTS

| | | | |
|---|---|---|---|
| 4,789,240 A | * 12/1988 | Bush | .......................... 356/477 |
| 5,394,488 A | 2/1995 | Fernald et al. | |
| 5,590,090 A | 12/1996 | Duggal et al. | |
| 5,636,181 A | * 6/1997 | Duggal | ........................ 356/484 |
| 6,008,900 A | * 12/1999 | Green et al. | ........... 250/227.27 |
| 6,233,052 B1 | * 5/2001 | Zare et al. | ................... 250/343 |

FOREIGN PATENT DOCUMENTS

| | | |
|---|---|---|
| EP | 0 342 337 A | 11/1989 |
| EP | 0 895 072 A | 2/1999 |
| GB | 2 209 221 A | 5/1989 |
| JP | 10-501893 | 2/1998 |
| WO | WO 96/30731 | 10/1996 |

OTHER PUBLICATIONS

High Frequency Ultrasound Imaging Using An Active Optical Detector by James D. Hamilton et al. Appears in IEEE Transactions on Ultrasaonics, Feroelectorics, and Frequench Control, vol. 45, No. 3, May 1998.
Patent Abstract of Japan vol. 1998, No. 01, Jan. 30, 1998 & JP 09 229718 A (Oki Electri Ind. Co. Ltd.), Sep. 5, 1997 (Abstracts).

* cited by examiner

*Primary Examiner*—Paul Ip
*Assistant Examiner*—Hung T Vy
(74) *Attorney, Agent, or Firm*—Sughrue Mion, PLLC (57) ABSTRACT

A dynamic change detecting apparatus allows canceling the influence of environmental change or an individual difference between a plurality of laser elements so as to perform a stable detection. This apparatus has a laser, including a laser resonator, for emitting a laser beam while causing frequency modulation in accordance with dimensional change of the laser resonator; a partial reflection mirror for splitting the laser beam emitted by the laser into a plurality of split-beams and guiding the plurality of split-beams to a plurality of optical paths having mutually different optical path lengths respectively; a frequency shifter for causing frequency shift in at least one of the plurality of split-beams; a lens for combining the plurality of split-beams with each other to obtain interference light; an photodetector for detecting the interference light to obtain an intensity signal; a demodulation unit for demodulating the intensity signal to generate a demodulated signal; and an integration processing unit for obtaining a signal corresponding to the dynamic change on the basis of the demodulated signal.

20 Claims, 9 Drawing Sheets

DYNAMIC CHANGE DETECTING METHOD, DYNAMIC CHANGE DETECTING APPARATUS AND ULTRASONIC DIAGNOSTIC APPARATUS

BACKGROUND OF THE INVENTION

1. Field of the Invention

The present invention relates to a method and an apparatus for detecting dynamic change in ultrasonic wave or the like propagating through a medium. Further, the present invention relates to an ultrasonic diagnostic apparatus having such a dynamic change detecting apparatus.

2. Description of a Related Art

In an ultrasonic diagnostic apparatus for a so-called ultrasonic echo observation or the like, it is the general practice to use piezoelectric materials typically represented by PZT (Pb (read) zirconate titanate) for an ultrasonic sensor portion (probe).

Figure 12A:
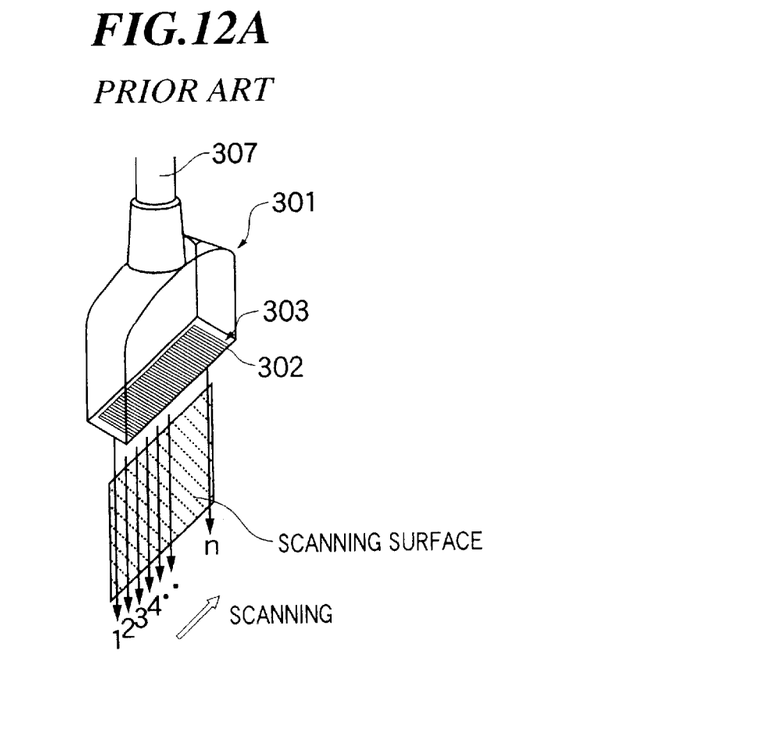
FIG. 12A and FIG. 12B schematically show the structure of a conventional probe.
Figure 12B:
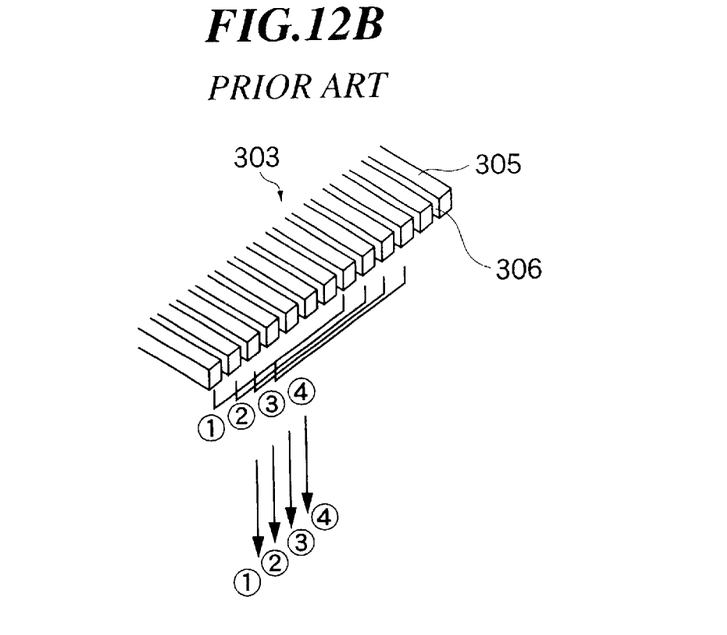

FIGS. 12A and 12B schematically show the structure of a conventional probe. FIG. 12A is a whole perspective view of the probe, and FIG. 12B is an enlarged perspective view of array vibrator included in the probe.

As shown in FIG. 12A, the probe 301 has a thin box shape as a whole, and has a slender rectangular probing surface 302. The probing surface 302 is brought into contact with a human body and an ultrasonic wave is transmitted so as to receive an ultrasonic echo reflected from the depths of the body. A cable 307, which transmits a drive signal for transmitting an ultrasonic wave and a detection signal of the ultrasonic wave, is connected to the upper side of the probe 301.

A comb-shaped array vibrator 303 serving as both a transmitter and a receiver of ultrasonic wave is housed in the probing surface 302. As shown in FIG. 12B, the array vibrator 303 is provided a number of slits 306 (having a width of, for example, 0.1 mm) in a thin strip-shaped PZT sheet (having a thickness of, for example, 0.2 to 0.3 mm) so as to form a number of (for example, 256) comb-teeth-shaped individual vibrator 305 (having, for example, a width of 0.2 mm and a length of 20 mm).

An electrode is formed in each individual vibrator 305, and a signal line is connected thereto. An acoustic lens layer or an acoustic matching layer made of resin material such as rubber is attached to the surface side (lower side in the drawing) of the array vibrator 303, and a backing material is attached to the back side. The acoustic lens layer converges the transmitted ultrasonic waves effectively. The acoustic matching layer improves the transmission efficiency of ultrasonic waves. The backing material has a function of holding the vibrator and causes vibration of the vibrator to be finished earlier.

Such ultrasonic probe and ultrasonic diagnostic apparatus are described in detail in "Ultrasonic Observation Method and Diagnostic Method", Toyo Publishing Co., or "Fundamental Ultrasonic Medicine", Ishiyaku Publishing Co.

In the field of ultrasonic diagnostic, it is desired to collect three-dimensional data in order to obtain more detailed information about the interior of an object's body. In order to comply with such a demand, it is required to make ultrasonic detecting elements (ultrasonic sensors) into a two-dimensional array. In the aforementioned PZT, however, it is difficult to fine the devices down and integrate them in the present conditions for the following reasons. That is, processing technology of PZT materials (ceramics) is almost on a limit level, and further fining down leads to an extreme decrease in processing yield. Moreover, if the number of wires increases, electrical impedance of the element and crosstalk between the elements (individual vibrators) would increase. It is therefore considered difficult to realize a two-dimensional array probe using PZT at the present level of the art.

On the other hand, Japanese patent application publication JP-A-10-501893 discloses an ultrasonic detecting apparatus including an array of vertical cavity surface emission laser (VCSEL) excited electrically (pumping). A cavity length of each laser is modulated by the acoustic field propagated from an object. As a result, the laser beam obtained thereby is frequency modulated by the acoustic field. The modulated laser beam is converted into amplitude modulation signal by a detector head, and thereafter, detected by a CCD array. Then, information of the signal is transmitted electrically to the signal processing assembly and processed. It is stated that this ultrasonic apparatus can achieve high level detection of frequency bandwidth, high resolving power of space and simplification of electric wiring.

Further, a paper entitled "High Frequency Ultrasound Imaging Using an Active Photodetector" by James D. Hamilton et al. appears in IEEE TRANSACTIONS ON ULTRASCONICS, FERROELECTRICS, AND FREQUENCY CONTROL, VOL. 45, NO. 3, MAY 1998. This paper discloses an ultrasonic detecting apparatus including laser and optical modulator having a waveguide made of neodymium doped glass.

However, the detection system using change in a length of the laser resonator due to the ultrasonic wave have no practicality without compensation for environmental changes such as temperature change because such a detection system has high sensitivity for displacement. In the case of arraying the sensors, since variance will be inevitably generated in oscillation frequencies at respective laser element, it would be difficult to put the sensors to practical use as an array, unless a measuring method which is not affected by the variance in oscillation frequencies of laser elements is used.

SUMMARY OF THE INVENTION

The present invention has been accomplished in view of these problems. A first object of the present invention is to provide a dynamic change detecting method and apparatus for detecting dynamic change stably by canceling influence of environmental change or an individual difference between a plurality of laser elements. A second object of the present invention is to provide an ultrasonic diagnostic apparatus using such a dynamic change detecting apparatus and appropriate for collection of three-dimensional data.

In order to solve the aforementioned problems, a dynamic change detecting method according to the present invention comprises steps of: (a) emitting a laser beam while causing frequency modulation to the laser beam to be generated in accordance with change in a size of a laser resonator by propagating the dynamic change to a total reflection mirror included in the laser resonator to cause dynamic displacement to the total reflection mirror; (b) separating the laser beam into a plurality of split-beams and guiding the plurality of split-beams to a plurality of optical paths having mutually different optical path lengths, respectively; (c) causing frequency shift in at least one of the plurality of split-beams; (d) combining the plurality of split-beams with each other to obtain interference light, and detecting the interference light to obtain an intensity signal corresponding to intensity of the interference light; (e) demodulating the intensity signal to generate a demodulated signal; and (f) obtaining a signal corresponding to the dynamic change on the basis of the demodulated signal.

Moreover, a dynamic change detecting apparatus according to the present invention comprises a laser including a laser resonator having a total reflection mirror where a dynamic perturbation is generated by propagation of dynamic change, the laser emitting a laser beam while causing frequency modulation to the laser beam to be generated in accordance with change in a size of the laser resonator; first means for separating the laser beam emitted from the laser into a plurality of split-beams and guiding the plurality of split-beams to a plurality of optical paths having mutually different optical path lengths, respectively; second means for causing frequency shift in at least one of the plurality of split-beams; third means for combining the plurality of split-beams with each other to obtain interference light; a photodetector for detecting the interference light to obtain an intensity signal corresponding to intensity of the interference light; fourth means for demodulating the intensity signal to generate a demodulated signal; and fifth means for obtaining a signal corresponding to the dynamic change on the basis of the demodulated signal.

Further, an ultrasonic diagnostic apparatus according to the present invention comprises transmitting means for transmitting an ultrasonic wave; receiving means for receiving an ultrasonic echo to convert the ultrasonic echo into an electric signal, the receiving means comprising a laser, including a laser resonator having a total reflection mirror where a dynamic perturbation is generated by propagation of dynamic change, for emitting a laser beam while causing frequency modulation to the laser beam to be generated in accordance with change in a size of the laser resonator, means for separating the laser beam emitted from the laser into a plurality of split-beams and guiding the plurality of split-beams to a plurality of optical paths having mutually different optical path lengths respectively, means for causing frequency shift in at least one of the plurality of split-beams, means for combining the plurality of split-beams with each other to obtain interference light; a photodetector for detecting the interference light to obtaining an intensity signal corresponding to intensity of the interference light, means for demodulating the intensity signal to generate a demodulated signal, and means 45 for obtaining a signal corresponding to the dynamic change on the basis of the demodulated signal; and image processing and displaying means for image processing of the signal corresponding to the dynamic change and displaying an image on the basis of the signal.

According to the present invention, the separated laser beams pass through the optical paths having different optical path lengths respectively and the frequency shift is generated in at least one of the separated laser beams, and thereafter, the separated laser beams are combined with each other so as to cause interfere light (so-called heterodyne interference) even if the detection environment, for instance, the temperature is changed in the laser resonator. Therefore, intensity of the interfere light is hardly affected by the temperature change and the dynamic change of an object can be detected stably. In addition, in the case where the laser resonator is constructed as an array, the dynamic change of an object can be detected stably even if oscillation frequencies of respective resonator units have dispersion.

DESCRIPTION OF THE PREFERRED EMBODIMENTS

Now, embodiments of the present invention will be described in detail with reference to the drawings. The same reference numerals designate the same components, and explanation about the same components is omitted.

Figure 1:
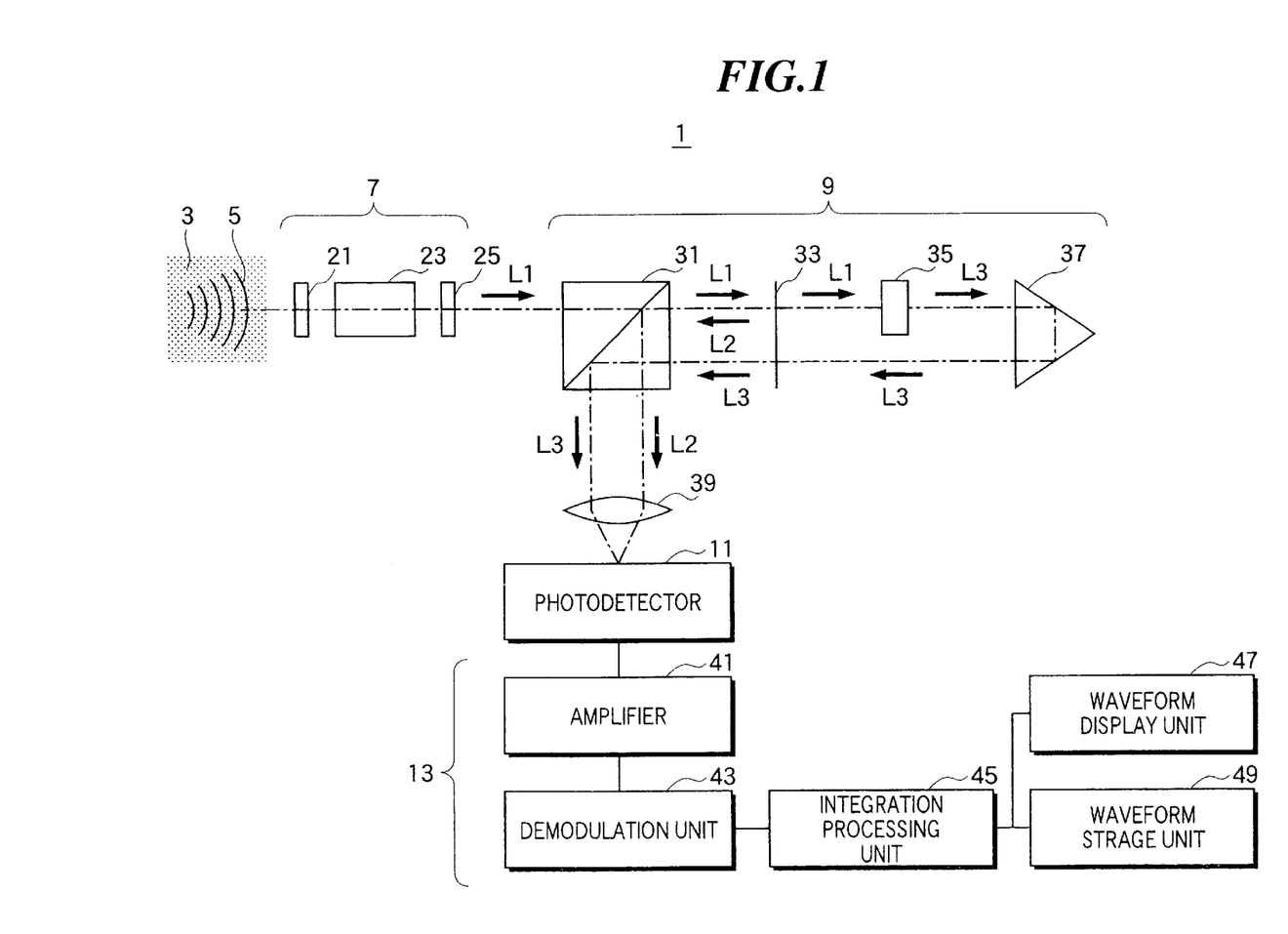
FIG. 1 is a diagram schematically showing a dynamic change detecting apparatus (ultrasonic detecting apparatus) according to a first embodiment of the present invention.

FIG. 1 is a diagram showing a dynamic change detecting apparatus (ultrasonic detecting apparatus) according to a first embodiment of the present invention.

This dynamic change detecting apparatus 1 includes a laser 7 having a laser resonator and receives an ultrasonic wave 5 propagating in an object 3 at a total reflection mirror 21 of the laser resonator. Laser light L1 emitted from the laser 7 is incident upon a heterodyne interference optical system 9, and the light having passed through the heterodyne interference optical system 9 is detected by an photodetector 11. An electric signal output from the photodetector 11 is conducted various processing in an electric signal processing unit 13.

The laser 7 has a total reflection mirror 21, a chamber 23 housing laser medium and so on, and a partial reflection mirror 25, which are arranged from the left to the right in the drawing. This laser 7 is excited by electricity, lamp, laser light, or the like.

An ultrasonic wave 5, which is propagating in an object 3 to be inspected (human body, for instance) from the left side in the drawing, is received by the total reflection mirror 21. An acoustic matching layer or a seal layer is disposed on the surface of the total reflection mirror 21. In the laser 7, the propagation of the ultrasonic wave 5 causes dynamic displacement of the total reflection mirror 21, which in turn causes perturbation in the optical resonator formed by the total reflection mirror 21 and the partial reflection mirror 25 so that the laser light L1 emitted from the laser 7 is frequency-modulated. The detail of modulation process of sound against light in the laser 7 will be described after, referring to FIG. 2.

In this embodiment, laser 7 of an external resonator type wherein an optical resonator is arranged outside a chamber 23 enclosing laser medium and so on is used. In this case, the perturbation due to the ultrasonic wave is propagated only to the total reflection mirror 21. Alternatively, a resonator LD of a vertical type (surface-emission laser) for emitting light in a direction perpendicular to the composition direction of the chamber 23 may be used. In this case, the composition of the optical resonator including the chamber 23 can be shortened. If length of the optical resonator is equal to or less than ½ of the ultrasonic wavelength, the whole optical resonator receives perturbation due to the ultrasonic waves so that the length of the optical resonator is extended or shortened.

Laser light L1 emitted from the laser 7 is incident upon the heterodyne interference optical system 9. A beam splitter 31 is disposed on the nearest position to the laser 7 in the heterodyne interference system 9. The laser light L1 is partially reflected and partially passes through the beam splitter 31. A partial reflection mirror 33 is disposed beyond the beam splitter 31. The partial reflection mirror 33 reflects light L2 that is a part of the laser light L1. A part of reflected light L2 is reflected downward in the drawing by the beam splitter 31.

A frequency shifter 35 including an acoustic optical module (AOM) or the like is disposed at the exit side of the partial reflection mirror 33. The frequency shifter 35 shifts a frequency of the incident light L1 slightly. The laser light L1 having passed through the partial reflection mirror 33 is frequency-shifted by the frequency shifter 35 and becomes light L3.

A reflection prism 37 is disposed at the exit side of the frequency shifter 35. The reflection prism 37 reflects the frequency-shifted light L3 to the left side.

A part of the light L3 passes through the partial reflection mirror 33 and is reflected downward in the drawing by the beam splitter 31.

The light L2 and the light L3 both reflected downward by the beam splitter 31 are converged on the photodetector by a lens 39 and combined with each other so that they interfere with each other on the photodetector 11. The photodetector 11 converts intensity (amplitude) of the interference light into an electric signal.

The electric signal output from photodetector 11 is transmitted to an electric signal-processing unit 13 and processed.

The electric signal processing unit 13 includes an amplifier 41 for amplifying the electric signal output from photodetector 11, a demodulating unit 43 for demodulating the amplified signal, an integration processing unit 45 for integrating the demodulated signal, a waveform display unit 47 for displaying the integrated signal as a waveform, and a waveform storage unit 49 for storing the waveform.

Figure 2:
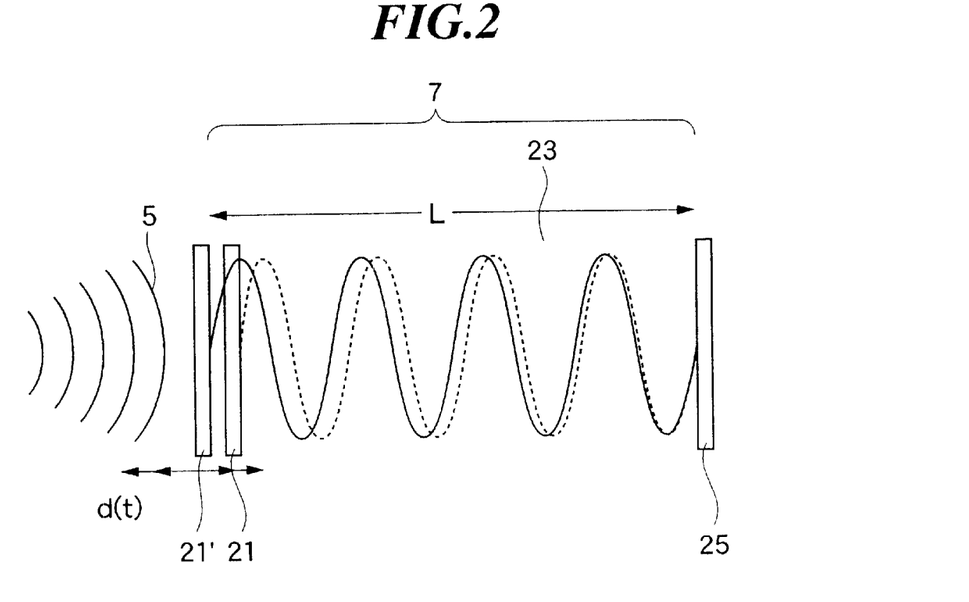
FIG. 2 is an enlarged schematic view showing displacement of a part of a laser resonator included in the dynamic change detecting apparatus as shown in FIG. 1.

FIG. 2 is an enlarged schematic view showing displacement of a part of a laser resonator included in the dynamic change detecting apparatus as shown in FIG. 1. In FIG. 2, reflection mirror 21, laser medium 23 and partial reflection mirror 33 of the laser 7 are shown. The ultrasonic wave 5 is received by the total reflection mirror 21, and the total reflection mirror 21 vibrates in the right and left directions in the drawing. As a result, the length L of the resonator varies. Here, change of the resonator length L, that is, displacement of the total reflection mirror of the resonator is supposed to be d(t).

When the total reflection mirror of the laser resonator shifts by d(t) due to the ultrasonic wave, the frequency ν (t) of the laser oscillation deviates, and this deviation Δν (t) is expressed as follows:

$$\Delta\nu(t) = -\nu_c \cdot \frac{d(t)}{L} \tag{1}$$

Out of laser light L1 incident upon the heterodyne interference optical system 9 as shown in FIG. 1, the light L2, which has been transmitted through the beam splitter 31 and reflected by the partial reflection mirror 33, is thereafter reflected from the beam splitter 31 so as to be incident upon the photodetector 11 through a lens 39. Consequently, the laser light L2 in a state where an ultrasonic wave is received to generate dynamic change in the total reflection mirror 21 can be expressed as follows:

$$f_1(t) = \cos\{2\pi\nu(t)\cdot t + \phi_1\} \tag{2}$$

where $\phi_1$ designates an initial phase.

On the other hand, the light L3 having passed through the partial reflection mirror 33 and the frequency shifter 35 is reflected from a reflection prism 37 and thereafter transmitted again through the partial reflection mirror 33. Then, the light L3 is reflected by the beam splitter 31 and incident upon the photodetector 11 through the lens 39. Supposing that ΔX represents a difference of optical pass lengths between light L2 and light L3, a time delay Δt=Δx/c is generated between light L2 and light L3 both incident upon the photodetector 11. Where, "c" represents a velocity of the light. Therefore, the light L3 is expressed as follows:

$$f_2(t) = \cos\{(\Omega_0 + 2\pi\nu(t-\Delta t))\cdot t + \phi_2\} \tag{3}$$

where $\Omega_0$ represents an amount of change in a shifted angular frequency caused by frequency shifter 35 and $\phi_2$ represents an initial phase.

Supposing that Δν represents a difference between the oscillation frequency ν (t) at the time "t" and the oscillation frequency ν (t−Δt) at the time (t−Δt), the following expression can be obtained.

$$\Delta\nu(t) = \nu(t) - \nu(t-\Delta t) \tag{4}$$

Consequently, it can be expressed as follows:

$$\nu(t-\Delta t) = \nu(t) - \Delta\nu(t) \tag{5}$$

Therefore, the expression (3) can be rewrote as follows:

$$f_2(t) = \cos\{(\Omega_0 + 2\pi(\nu(t) - \Delta\nu(t)))\cdot t + \phi_2\} \tag{6}$$

Since light L2 and light L3 are combined (superposed) with each other by the lens 39 on the photodetector 11, Light L2 and light L3 interfere with each other on the photodetector 11. From the expression (2) and (6), this superposition can be expressed as follows:

$$g(t) = f_1(t) + f_2(t) \quad (7)$$

$$= 2\cos\frac{1}{2}\{(\omega_0 + 2\pi(v(t) - \Delta v(t))) \cdot t + \phi_2 -$$

$$(2\pi v(t) \cdot t + \phi_1)\} \cdot \cos\frac{1}{2}\{(\omega_0 + 2\pi(v(t) - \Delta v(t))) \cdot$$

$$t + \phi_2 + (2\pi v(t) \cdot t + \phi_1)\}$$

$$= 2\cos\frac{1}{2}\{(\omega_0 - 2\pi\Delta v(t)) \cdot t + \phi_2 - \phi_1\} \cdot$$

$$\cos\frac{1}{2}\{(\omega_0 + 2\pi(2v(t) - \Delta v(t))) \cdot t + \phi_2 + \phi_1\}$$

Consequently, the amplitude variation A(t) generated by the superposition of light L2 and light L3 is expressed as follows:

$$A(t) = 2\cos\frac{1}{2}\{(\omega_0 - 2\pi\Delta v(t)) \cdot t + \phi_2 - \phi_1\} \quad (8)$$

Figure 3:
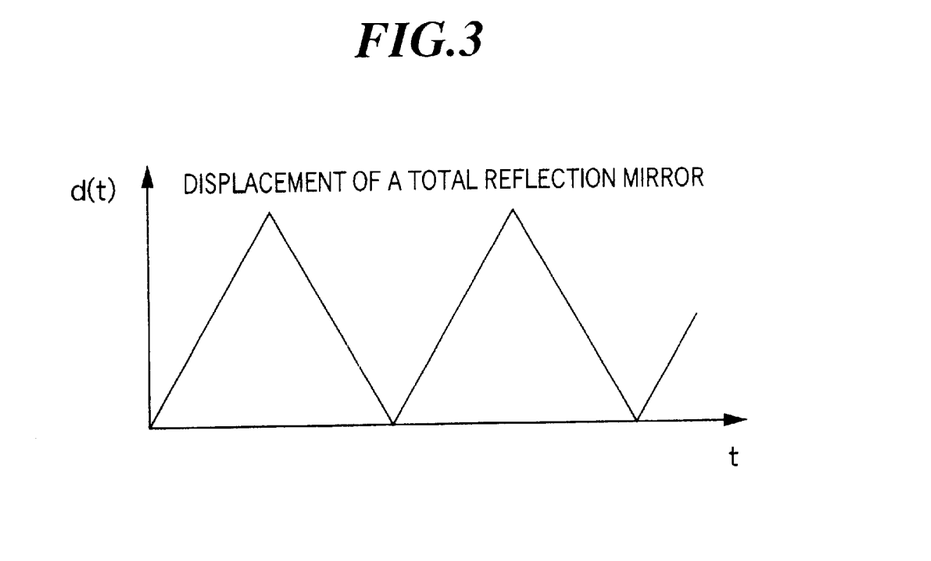
FIG. 3 is a graph showing an example of displacement of a reflection mirror included in the laser resonator oscillating due to propagation of an ultrasonic wave.
Figure 4:
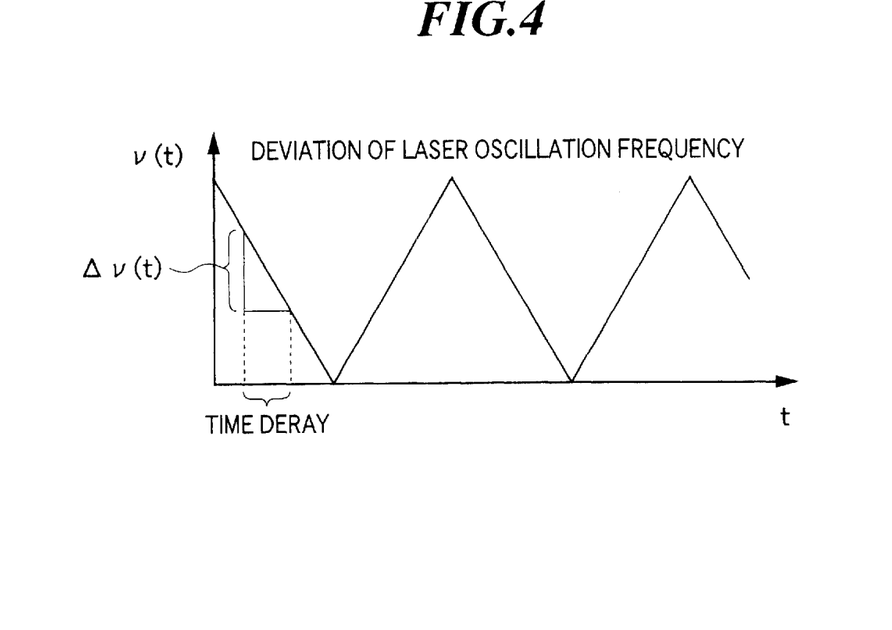
FIG. 4 is a graph showing the oscillation frequency v (t) of a laser beam oscillated from the laser resonator, when a reflection mirror in the laser resonator shifts with the displacement d(t) as shown in FIG. 3.
Figure 5:
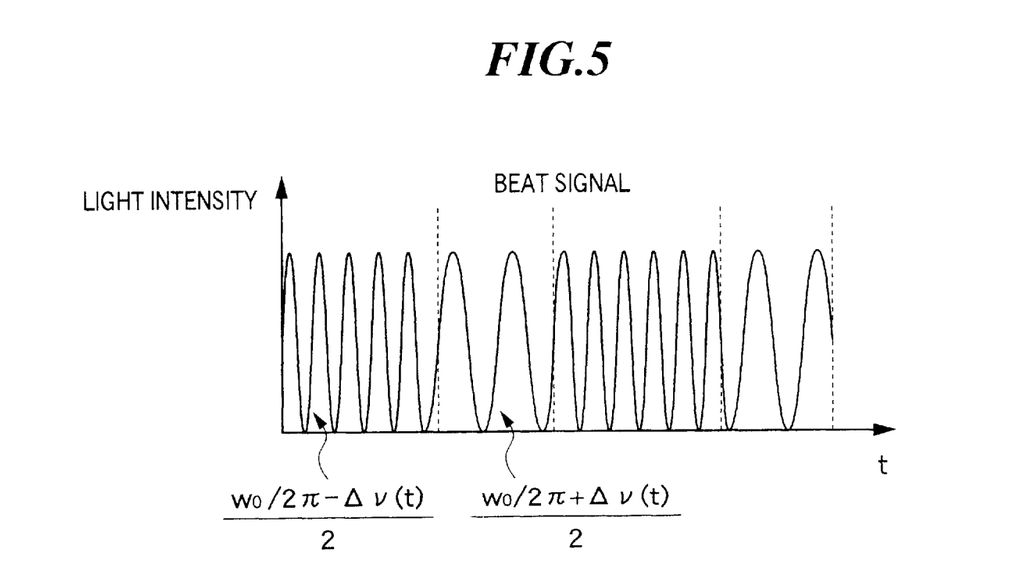
FIG. 5 is a graph showing a waveform of a beat signal in a photodetector when the reflection mirror in the laser resonator shifts with the displacement d(t) as shown in FIG. 3.

Now, for simplification, supposing that the ultrasonic waveform is a triangular waveform, the displacement d(t) of the total reflection mirror of the laser resonator 21 due to the ultrasonic wave is shown in FIG. 3. The deviation of the laser oscillation frequency v (t) becomes to have an opposite form to the displacement d(t) as shown in FIG. 4. When a light beam whose oscillation frequency is deviating with time as shown in FIG. 4 is incident upon an heterodyne interference optical system as shown in FIG. 1, an amplitude modulation having a frequency F(t) is generated. The frequency F(t) is shifted by an amount of change in the oscillation frequency corresponding to a time delay due to an optical path difference against the original frequency $\Omega_0/4\pi$ of heterodyne interference signal as a center frequency when the oscillation frequency is constant as shown in FIG. 5. Here, F(t) is expressed as follows:

$$F(t) = \frac{\omega_0/2\pi \pm \Delta v(t)}{2}$$

Figure 6:
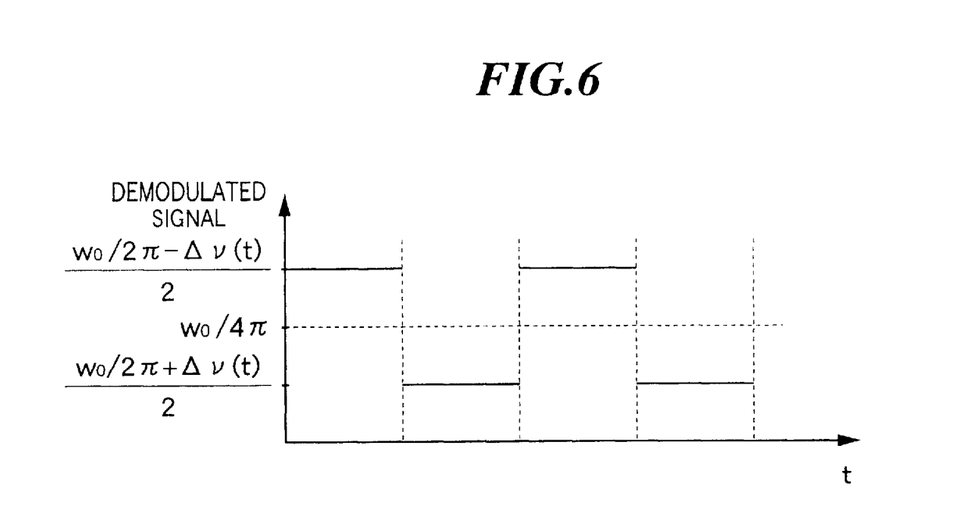
FIG. 6 is a graph showing a demodulated signal obtained by demodulating the beat signal as shown in FIG. 5.
Figure 7:
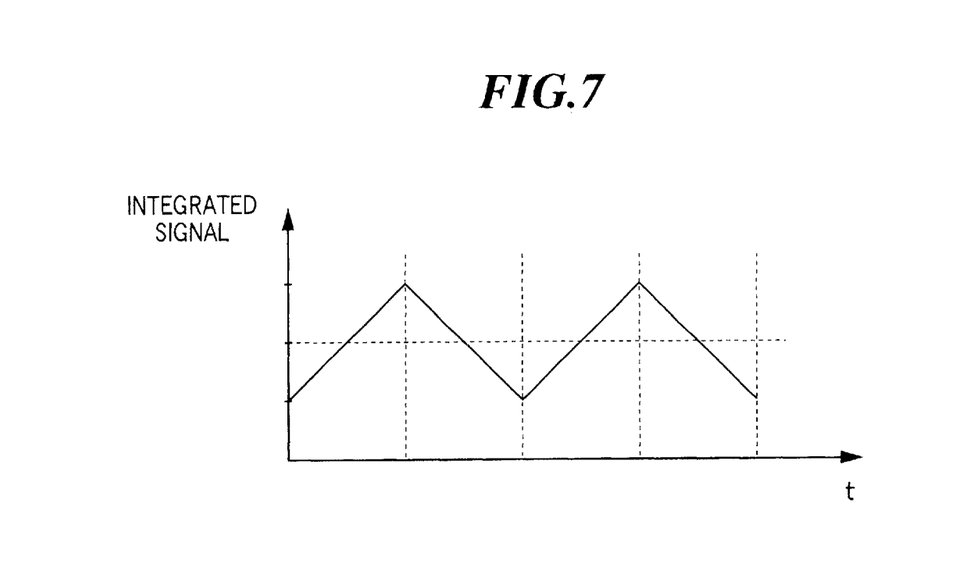
FIG. 7 is a graph showing the displacement d(t) of the reflection mirror in the laser resonator reproduced on the basis of the demodulated signal as shown in FIG. 6.

By detecting the light beam, an intensity signal corresponding to an intensity of the light, that is, a beat signal suffering the frequency modulation is obtained. Further, by demodulating the beat signal in the demodulation unit, the demodulated signal as shown in FIG. 6 can be obtained. The demodulated signal originally represents the change in the oscillation frequency corresponding to the time delay, and therefore, the displacement d(t) of the total reflection mirror 21 shift d(t) as shown in FIG. 7, that is, the ultrasonic waveform can be reproduced by conducting integration processing for the demodulated signal.

Dynamic change generated by various physical energy including an ultrasonic wave can be detected by displaying the waveform obtained by the integration processing on a display unit 47. Further, the waveform obtained by such processing may be stored in a storing unit 49.

For the matters concerning general signal processing in the electric signal processing unit 13, it may be referred to "Ultrasonic observation method and diagnostic method", Toyo Publishing Co., or "Fundamental ultrasonic medicine", Ishiyaku Publishing Co.

Figure 8:
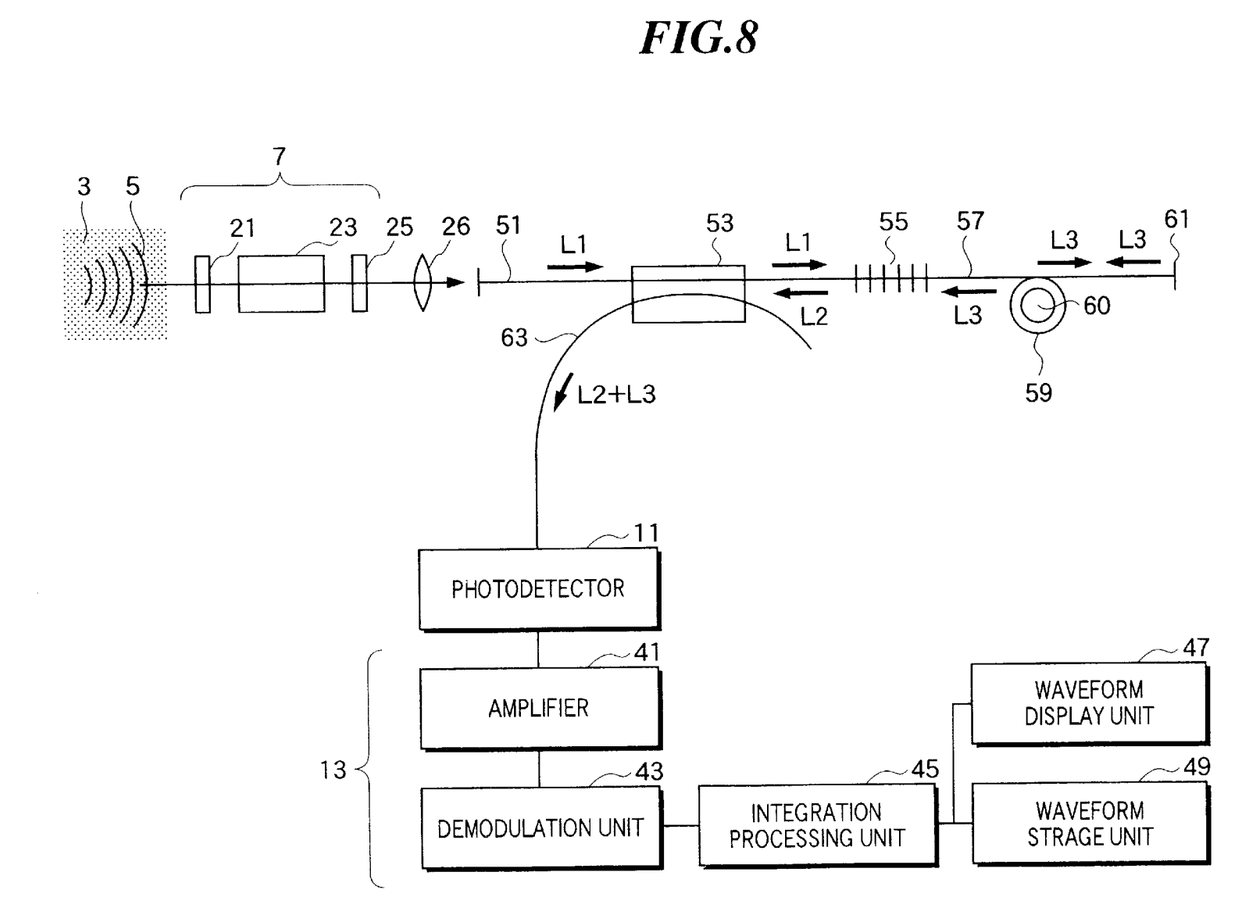
FIG. 8 is a diagram schematically showing a dynamic change detecting apparatus (ultrasonic detecting apparatus) according to a second embodiment of the present invention.

Next, a dynamic change detecting apparatus (ultrasonic detecting apparatus) according to a second embodiment of the present invention will be described referring to FIG. 8. FIG. 8 is a diagram schematically showing the apparatus.

A laser 7 similar to that in FIG. 1 is shown at the left end section as shown in FIG. 8. Light emitted from the laser 7 is incident upon an optical fiber 51 through a lens 26.

The optical fiber 51 extends to the right side in FIG. 8 passing through an optical coupler 53. An optical fiber Bragg grating 55 is connected to the end of the optical fiber 51. This grating 55 splits the incident light L1 into light L2 and light L3, similarly to the function of the partial reflection mirror 33 in the apparatus as shown in FIG. 1. A frequency shifter 59 is connected ahead of the grating 55. The frequency shifter 59, composed by winding an optical fiber 57 around a piezoelectric element 60, shifts the frequency of the light passing through the optical fiber 57 according to the variation of the piezoelectric element diameter. A total reflection mirror 61 is disposed ahead of the frequency shifter 59.

Light L2 reflected from the grating 55 and light L3 reflected from the total reflection mirror are superposed by the optical coupler 53, and incident upon an optical fiber 63. Further, the superposed light L2 and L3 are incident upon the photodetector 11 and converted into an electric signal. The following electric signal processing is performed similarly as in the apparatus as shown in FIG. 1.

Figure 9:
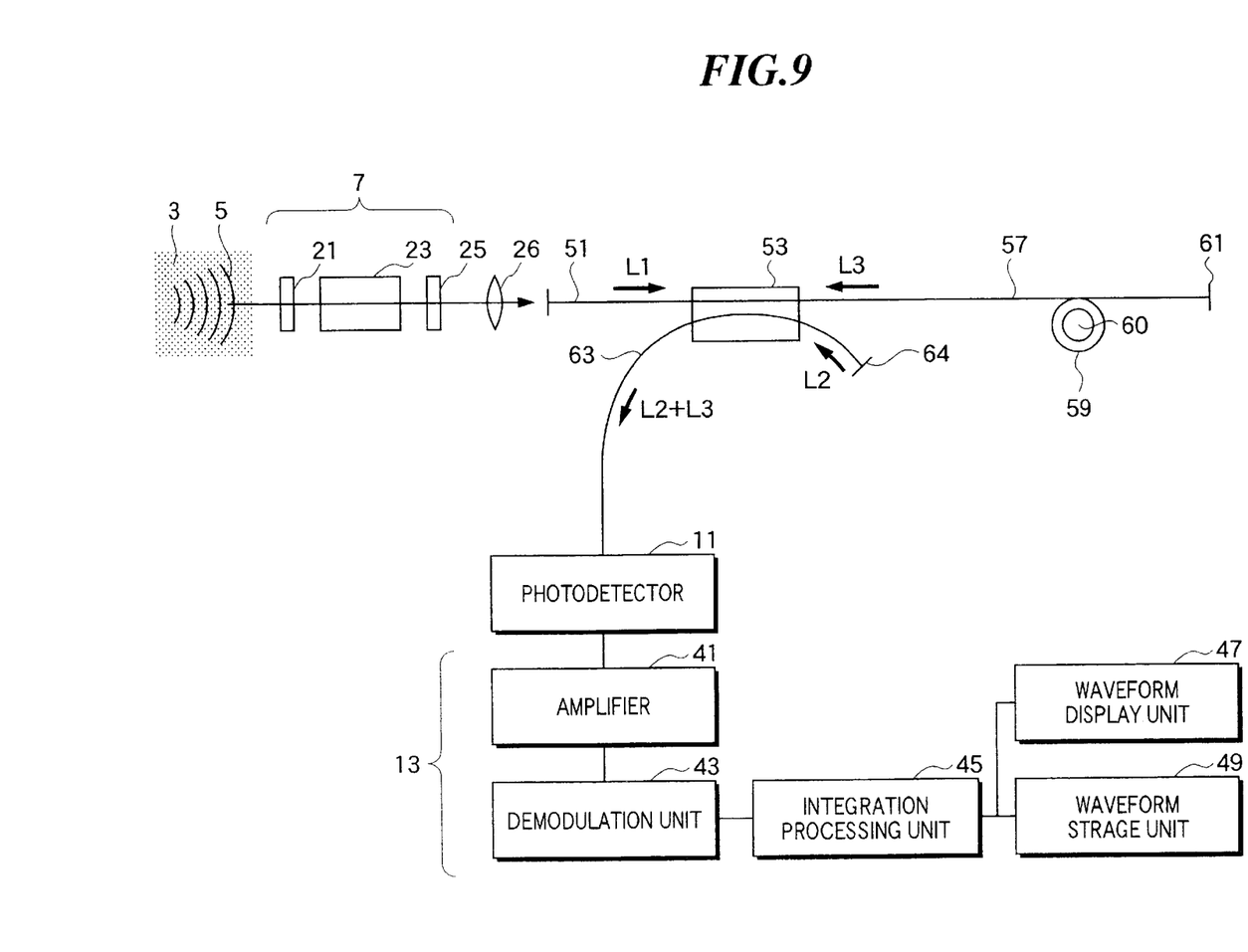
FIG. 9 is a diagram schematically showing a dynamic change detecting apparatus (ultrasonic detecting apparatus) according to a third embodiment of the present invention.

Next, a dynamic change detecting apparatus (ultrasonic detecting apparatus) according to a third embodiment of the present invention will be described referring to FIG. 9. FIG. 9 is a diagram schematically showing the apparatus.

In this dynamic change detecting apparatus, a total reflection mirror 64 is disposed at the end of the optical fiber 63 in place of the optical fiber Bragg grating 55 in the apparatus as shown in FIG. 8. Light L2, which is a part of light L1 emitted from the laser 7 and having passed through the optical fiber 51, is incident upon the optical fiber 63 at the optical coupler 53, and light L3, which is another part of the light L1, transmits in the optical fiber 51 as it is. The light L2 is reflected by the total reflection mirror 64. On the other hand, the light L3 is reflected by the total reflection mirror 61 and frequency-modulated by passing through the frequency shifter 59. Those light L2 and L3 are superposed in the optical coupler 52 to be transmitted in the optical fiber 63 and incident upon the photodetector 11. The other components of this apparatus are similar to the apparatus as shown in FIG. 1.

Figure 10:
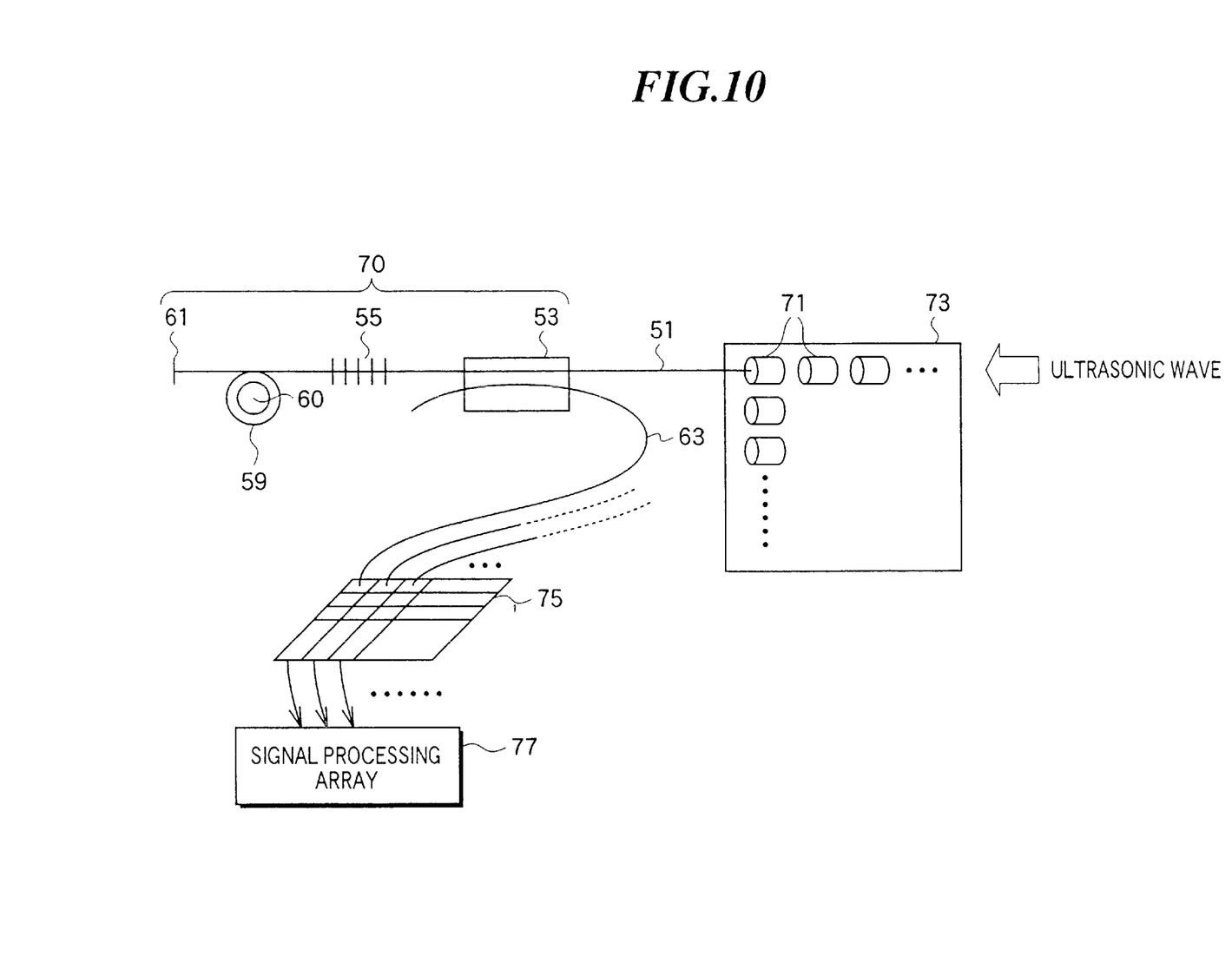
FIG. 10 is a diagram schematically showing a dynamic change detecting apparatus (ultrasonic detecting apparatus) having a surface-emitting laser array, according to a fourth embodiment of the present invention.

Next, a dynamic change detecting apparatus according to a fourth embodiment of the present invention will be described referring to FIG. 10. FIG. 10 is a schematic view showing the dynamic change detecting apparatus according to this embodiment.

In this dynamic change detecting apparatus, the dynamic change detecting systems, one of which is shown in FIG. 8, are composed to form an array. This dynamic change detecting apparatus has a surface emission laser array 73 wherein a number of laser reflection mirrors 71 are arranged in a matrix shape. A heterodyne interference optical system 70 similar to that in the dynamic change detecting apparatus as shown in FIG. 8 is connected to each laser reflection mirror 71. The interference light of each interference system 70 is transmitted to a photodetector array 75 through the optical fiber 63, and detected individually. The electric signals generated by the photodetector array 75 are transmitted to a signal-processing array 77 and processed.

By arraying the dynamic change detecting systems, scanning, deviation, or conversion of ultrasonic waves can be performed dynamically and simultaneously in parallel. Therefore, it becomes easy to collect three-dimensional data. In the dynamic change detecting apparatus, since signals are derived by using fine optical fibers, an array having high integration can be realized. Further, since light is used as a signal, the signal transmission impedance does not increase. Furthermore, such an apparatus may be realized by arraying the dynamic change detecting system as shown in FIG. 9.

Figure 11:
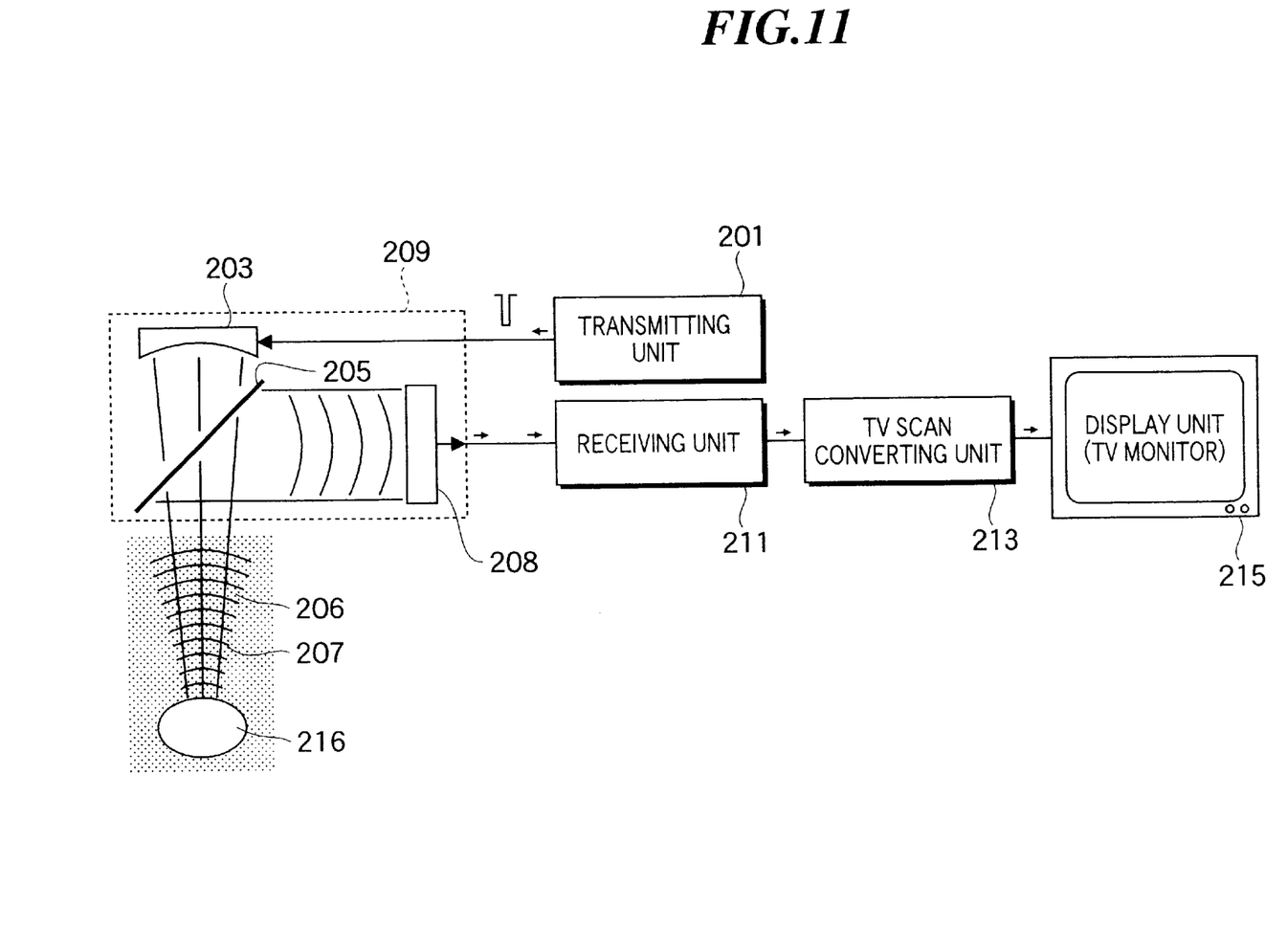
FIG. 11 is a block diagram showing an ultrasonic diagnostic apparatus according to one embodiment of the present invention.

Next, an ultrasonic diagnostic apparatus according to an embodiment of the present invention will be described referring to FIG. 11. FIG. 11 is a block diagram schematically showing the ultrasonic diagnostic apparatus.

This ultrasonic diagnostic apparatus includes a transmitting unit 201, a probe 209, a receiving unit 211, a TV scan converting unit 213 and a display unit (television monitor) 215.

The transmitting unit 201 transmits an ultrasonic drive signal of a pulse type to an ultrasonic transmission transducer 203 including PZT, PVDF, or the like. The transducer 203 transmits an ultrasonic wave and causes the ultrasonic wave to propagate into an object body 206. An ultrasonic partial reflection mirror 205 (a plate made of resin, or the like) is arranged on downside of the transducer 203 in the drawing. In the object body 206, an ultrasonic echo 207 reflected upward in the drawing from depth 216 of the object body 206 is reflected to the right side by a partial reflection mirror 205 in the probe 209 and incident upon an ultrasonic detecting unit 208 of a two-dimensional array type. The ultrasonic detecting unit 208 converts an ultrasonic wave into an optical signal and transmits it to a receiving unit 211. The receiving unit 211 converts the optical signal from the ultrasonic detecting unit 208 into an electric signal. The TV scan-converting unit 213 amplifies or otherwise processes the electric signal from the receiving unit 211, and thereafter, performs the imaging processing. The signal after the imaging processing is transmitted to the display unit (TV monitor) 215 and is displayed.

According to this embodiment, the effect of the environmental change or individual difference between a plurality of laser elements can be cancelled so as to provide a dynamic change detecting apparatus that performs a stable detection. Therefore, an ultrasonic diagnostic apparatus appropriate for three-dimensional data can be realized. By using such an ultrasonic diagnostic apparatus, a high-resolution image of internal of an object's body can be obtained.

Although embodiments of the present invention have been explained above referring to drawings, the present invention is not limited to the above embodiments and various additions or modifications can be made. In the above embodiments, the dynamic change to be detected is described as an ultrasonic wave propagating in an object as an example. However, according to the present invention, it is also possible to detect a sound wave, acceleration, distortion, temperature, displacement, or other phenomena.

What is claimed is:

1. A dynamic change detecting method comprising the steps of:
   (a) emitting a laser beam while causing frequency modulation to the laser beam to be generated in accordance with change in a size of a laser resonator by propagating the dynamic change to a total reflection mirror included in the laser resonator to cause dynamic perturbation to said total reflection mirror;
   (b) separating the laser beam into a plurality of split-beams and guiding said plurality of split-beams to a plurality of optical paths having mutually different optical path lengths, respectively;
   (c) causing frequency shift in at least one of said plurality of split-beams;
   (d) combining said plurality of split-beams with each other to obtain interference light;
   (e) detecting said interference light to obtain an intensity signal corresponding to intensity of the interference light;
   (f) demodulating the intensity signal to generate a signal corresponding to the dynamic change.

2. The dynamic change detecting method according to claim 1, wherein:
   step (b) includes separating the laser beam into a plurality of split-beams by using a partial reflection mirror; and
   step (d) includes combining said plurality of split-beams by using a lens.

3. The dynamic change detecting method according to claim 1, wherein:
   step (b) includes separating the laser beam into first and second split-beams by entering the laser beam into one end of a first optical fiber to transmit a part of incident light through an optical fiber Bragg grating formed at the other end of said first optical fiber and to reflect another part of the incident light from said optical fiber Bragg grating;
   step (c) includes entering the first split-beam into a second optical fiber connected to said first optical fiber with said optical fiber Bragg grating therebetween, and changing a frequency of the first split-beam passing through said second optical fiber in response to change in a diameter of a piezoelectric element around which said second optical fiber is wound; and
   step (d) includes combining the first and second split-beams with each other by using an optical coupler.

4. The dynamic change detecting method according to claim 1, wherein:
   step (b) includes separating the laser beam into first and second split-beams by entering the laser beam into a first optical fiber wherein a total reflection mirror is formed at an end thereof and entering a part of the laser beam passing though said first optical fiber into a second optical fiber wherein a total reflection mirror is formed at an end thereof by using an optical coupler;
   step (c) includes changing a frequency of the first split-beam passing through said first optical fiber in accordance with change in a diameter of a piezoelectric element around which said first optical fiber is wound; and
   step (d) includes combining the first and second split-beams with each other reflected and returned from total reflection mirrors formed at the ends of said first and second optical fibers respectively by using said optical coupler.

5. The dynamic change detecting method according to claim 1, wherein step (f) includes conducting integration processing for said demodulated signal.

6. The dynamic change detecting method according to claim 1, wherein said laser includes a laser of an external resonator type.

7. The dynamic change detecting method according to claim 1, wherein said laser includes a vertical resonator LD.

8. The dynamic change detecting method according to claim 1, wherein step (a) includes propagating the dynamic change of an object to a plurality of total reflection mirrors which constitute one of a one-dimensional array and a two-dimensional array.

9. The dynamic change detecting method according to claim 1, wherein said dynamic change includes an ultrasonic wave propagating in an object to be inspected.

10. A dynamic change detecting apparatus comprising:
    a laser including a laser resonator having a total reflection mirror where a dynamic perturbation is generated by propagation of a dynamic change, said laser emitting a laser beam while causing frequency modulation to the laser beam to be generated in accordance with change in a size of said laser resonator;

first means for separating the laser beam emitted from said laser into a plurality of split-beams and guiding said plurality of split-beams to a plurality of optical paths having mutually different optical path lengths, respectively;

second means for causing frequency shift in at least one of said plurality of split-beams;

third means for combining said plurality of split-beams with each other to obtain interference light;

a photodetector for detecting the interference light to obtain an intensity signal corresponding to intensity of the interference light; and demodulator means for demodulating the intensity signal to generate a signal corresponding to the dynamic change.

11. The dynamic change detecting apparatus according to claim 10, wherein:

said first means includes a partial reflection mirror for separating the laser beam into a plurality of split-beams; and said third means includes a lens for combining said plurality of split-beams with each other.

12. The dynamic change detecting apparatus according to claim 10, wherein:

said first means includes a first optical fiber where the laser beam emitted from said laser is incident upon one end thereof, an optical fiber Bragg grating formed at the other end of said first optical fiber and a second optical fiber connected to said first optical fiber with said optical fiber Bragg grating therebetween;

said second means includes a piezoelectric element, around which said second optical fiber is wound, for changing a frequency of light passing through said second optical fiber in accordance with change in a diameter of said piezoelectric element; and said third means includes an optical coupler and a third optical fiber for transmitting laser beams combined with each other by said optical coupler.

13. The dynamic change detecting apparatus according to claim 10, wherein:

said first means includes a first optical fiber upon which the laser beam emitted from said laser is incident wherein a total reflection mirror is formed at an end thereof and a second optical fiber wherein a total reflection mirror is formed at an end thereof;

said first and third means includes an optical coupler for separating the laser beam into a plurality of split-beams by entering a part of the laser beam passing through said first optical fiber into said second optical fiber, and for combining the plurality of split-beams reflected and returned from the total reflection mirrors formed at the ends of said first and second optical fibers, respectively; and said second means includes a piezoelectric element, around which said first optical fiber is wound, for changing a frequency of light passing through said first optical fiber in accordance with change in a diameter of said piezoelectric element.

14. The dynamic change detecting apparatus according to claim 10, wherein said demodulating means conducts integration processing for the demodulated intensity signal.

15. The dynamic change detecting apparatus according to claim 10, wherein said laser includes a laser of an external resonator type.

16. The dynamic change detecting apparatus according to claim 10, wherein said laser includes a vertical resonator LD.

17. The dynamic change detecting apparatus according to claim 10, wherein said laser includes a plurality of total reflection mirrors which constitute one of a one-dimensional array and a two-dimensional array.

18. The dynamic change detecting apparatus according to claim 10, wherein said dynamic change includes an ultrasonic wave propagating in an object to be inspected.

19. An ultrasonic diagnostic apparatus, comprising:

an ultrasonic transmitter operative to transmit an ultrasonic wave;

an ultrasonic receiver operative to receive an ultrasonic echo to convert the ultrasonic echo into an electric signal, said receiver comprising a laser, including a laser resonator having a total reflection mirror where a dynamic perturbation is caused by propagation of dynamic change, for emitting a laser beam while causing frequency modulation to the laser beam in accordance with change in a size of the laser resonator, a beam separator operative to separate the laser beam emitted from said laser into a plurality of split-beams and guiding said plurality of split-beams to a plurality of optical paths having mutually different optical path lengths respectively, a frequency shifter operative to cause a frequency shift in at least one of said plurality of split-beams, an optical combiner operative to combine said plurality of split-beams with each other to obtain interference light; a photodetector for detecting the interference light to obtain an intensity signal corresponding to intensity of the interference light, and demodulator operative to demodulate the intensity signal to generate a signal corresponding to the dynamic change;

an image processor for image processing the signal corresponding to the dynamic change; and a display for displaying an image on the basis of the signal image processed by the image processor.

20. The ultrasonic diagnostic apparatus according to claim 19, wherein said laser includes a plurality of total reflection mirrors which constitute one of a one-dimensional array and a two-dimensional array.

* * * * *